(12) United States Patent
Burns et al.

(10) Patent No.: US 7,518,027 B2
(45) Date of Patent: Apr. 14, 2009

(54) PRODUCTION OF OLEFINS

(75) Inventors: Andrew Lindsay Burns, Kinross (GB); David Charles Griffiths, Esher (GB); William Terence Woodfin, North Waltham (GB)

(73) Assignee: Innovene Europe Limited, Middlesex (GB)

( * ) Notice: Subject to any disclaimer, the term of this patent is extended or adjusted under 35 U.S.C. 154(b) by 602 days.

(21) Appl. No.: 10/502,846

(22) PCT Filed: Feb. 6, 2003

(86) PCT No.: PCT/GB03/00498

§ 371 (c)(1),
(2), (4) Date: Jul. 29, 2004

(87) PCT Pub. No.: WO03/066551

PCT Pub. Date: Aug. 14, 2003

(65) Prior Publication Data
US 2005/0020868 A1    Jan. 27, 2005

(30) Foreign Application Priority Data
Feb. 9, 2002    (GB) .................... 0203058.3

(51) Int. Cl.
*C07C 5/327*    (2006.01)
*C07C 5/333*    (2006.01)

(52) U.S. Cl. .............. 585/658; 585/651; 585/652; 585/653; 585/660; 585/661; 585/662; 585/663

(58) Field of Classification Search ............ 585/658, 585/660–663, 324, 651–653
See application file for complete search history.

(56) References Cited

FOREIGN PATENT DOCUMENTS

| | | |
|---|---|---|
| EP | 0 127 220 | 12/1984 |
| EP | 0 142 887 | 5/1985 |
| EP | 0 209 980 | 1/1987 |
| EP | 0 261 870 | 3/1988 |
| EP | 0 332 289 B1 | 9/1989 |
| EP | 0 529 793 A2 | 3/1993 |
| EP | 0 709 446 A2 | 5/1996 |
| GB | 2 125 062 A | 2/1984 |
| GB | 2 130 113 A | 5/1984 |
| GB | 2 146 350 A | 4/1985 |
| WO | WO 9404532 A1 | 3/1994 |
| WO | WO 00/14035 | 3/2000 |
| WO | WO 00/15587 | 3/2000 |
| WO | WO 01 83405 A1 | 11/2001 |

*Primary Examiner*—In Suk Bullock
(74) *Attorney, Agent, or Firm*—Nixon & Vanderhye P.C.

(57) ABSTRACT

A process for the production of a mono-olefin from a feedstock comprising a paraffinic hydrocarbon which process comprises a) partially combusting at a pressure of at least (15) barg a mixture of the hydrocarbon feed and a molecular oxygen-containing gas in contact with a catalyst capable of supporting combustion beyond the normal fuel rich limit of flammability where they are reacted to form a product comprising one or more mono-olefin(s), carbon monoxide and hydrogen and b) recovering the one or more olefin(s).

19 Claims, 5 Drawing Sheets

PRODUCTION OF OLEFINS

This application is the U.S. National Phase of International Application PCT/GB03/00498, filed 6 Feb. 2003, which designated the U.S.

The present invention relates to a process for the production of olefins from hydrocarbons, more particularly to an energy-efficient process in which the hydrocarbons are treated to autothermal cracking.

Olefins (ethylene, propylene and butenes) production is a very energy-intensive process. Current steam cracking technology involves a process furnace to provide energy to crack feeds to olefin products, heat recovery from the products, a large compressor to pressurise the product stream to relatively high pressures (3-500 psig), and distillation to separate and purify the products. The process furnace is a relatively inefficient way to provide the heat of cracking: only about 40 to 50% of the heat released in the process furnace is used in the cracking reactions. The remainder of the furnace heat is recovered in the furnace convective section and integrated with the process gas heat recovery systems to provide high pressure steam to drive the reactor effluent and refrigeration compressors. Any additional energy (in the form of high pressure steam) is typically provided by auxiliary boilers. Steam cracking suffers from the disadvantage that providing compressor energy through such a steam cycle is thermodynamically inefficient, converting only about 25% of the thermal energy of the fuel into useful shaftwork. This, combined with the low efficiency of the process furnace, makes the production of olefins very fuel-intensive.

Autothermal cracking is a new route to olefins in which the hydrocarbon feed is mixed with oxygen and passed over an autothermal cracking catalyst. Combustion is initiated on the catalyst surface and the heat required to raise the reactants to process temperature and to carry out the endothermic cracking process is generated in situ. As a result, there is no need for a process furnace. Such a process is described for example in EP 332289B; EP-529793B; EP-A-0709446 and WO 00/14035.

Unlike conventional cracking, autothermal cracking produces carbon monoxide in significant quantities depending upon the prevailing reaction conditions. Therefore the product stream contains not only a range of paraffinic and olefinic components but also significant quantities of hydrogen and carbon monoxide.

Autothermal cracking is typically conducted at low pressure in order to ensure adequate selectivity towards the desired products rather than to carbon monoxide. However it has now been found that the autothermal cracking process can be operated at high pressure and that the loss in selectivity towards olefins is not as pronounced as one would expect.

Furthermore it has now been found that if the feedstock costs are very low, for example where there is a very cheap supply of hydrocarbon, then the need for high selectivity is less great. Given that the loss in selectivity towards olefins is not as pronounced as expected the auto thermal cracking reaction may be operated at high pressure with economical benefits.

Operating autothermal cracking at high pressure reduces the degree of compression required to pressurise the product stream to facilitate the separation and purification of the olefin products. This improves the economics of the process both in terms of reduced overall power requirements and savings in process equipment. In certain circumstances it is possible to operate the autothermal cracking process at sufficiently high pressure to completely eliminate the need for downstream compression.

Thus the first embodiment of the present invention provides a process for the production of a mono-olefin from a feedstock comprising a paraffinic hydrocarbon which process comprises
  a) partially combusting at a pressure of at least 15 barg a mixture of the hydrocarbon feed and a molecular oxygen-containing gas in contact with a catalyst capable of supporting combustion beyond the normal fuel rich limit of flammability where they are reacted to form a product comprising one or more mono-olefin(s), carbon monoxide and hydrogen and
  (b) recovering the one or more olefin(s).

Preferably step (b) comprises separating the product from step (a) into a stream comprising carbon monoxide and hydrogen and a stream comprising one or more olefins and recovering the one or more olefin(s).

The product stream resulting from step (a) may comprise carbon dioxide which is usually removed prior to the separation in step (b).

The product stream resulting from step (a) may comprise methane. Wherein the product stream from step (a) comprises methane step (b) usually involves separating the product stream into a stream comprising carbon monoxide, hydrogen and methane and a stream comprising one or more olefins and then recovering the one or more olefin(s).

The stream comprising carbon monoxide, hydrogen and optionally methane may be used as a fuel. However this represents a waste of a valuable resource and therefore imposes an economic penalty on the process. A solution to this problem is to pass this stream to a Fischer-Tropsch reactor wherein at least part of the carbon monoxide and hydrogen is converted to higher value products and wherein the stream comprises any methane the methane passes through the Fischer-Tropsch reactor unreacted.

Thus a second embodiment of the invention provides a process for the production of a mono-olefin from a feedstock comprising a paraffinic hydrocarbon which process comprises
  a) partially combusting at a pressure of at least 15 barg a mixture of the hydrocarbon feed and a molecular oxygen-containing gas in contact with a catalyst capable of supporting combustion beyond the normal fuel rich limit of flammability where they are reacted to form a product comprising one or more mono-olefin(s), carbon monoxide and hydrogen
  (b) separating the product from step (a) into a stream comprising carbon monoxide and hydrogen and a stream comprising one or more olefins and recovering the one or more olefin(s),
  (c) passing the stream comprising carbon monoxide and hydrogen separated in step (b) to a Fischer-Tropsch reactor containing a Fischer-Tropsch catalyst wherein at least part of said stream is converted to hydrocarbons, and thereafter recovering at least a part of the hydrocarbon product.

In a third embodiment of the invention the carbon dioxide may be initially removed from the product stream produced in step (a) and the resultant product may then be separated into a stream comprising carbon monoxide and hydrogen and a stream comprising one or more olefins. The carbon dioxide may then be combined with the stream comprising carbon monoxide and hydrogen and passed over a low temperature water gas shift catalyst to convert carbon dioxide and hydrogen into carbon monoxide and water. The carbon monoxide along with hydrogen may then be passed to a Fischer-Tropsch reactor Thus the third embodiment of the invention provides a process for the production of a mono-olefin from a feedstock comprising a paraffinic hydrocarbon which process comprises the steps of:

(a) partially combusting at a pressure of at least 15 barg a mixture of the hydrocarbon feed and a molecular oxygen-containing gas in contact with a catalyst capable of supporting combustion beyond the normal fuel rich limit of flammability, where they are reacted to form a product comprising one or more mono-olefin(s), carbon monoxide, hydrogen and carbon dioxide and removing the carbon dioxide from the product stream (b) separating the product stream of step (a) into a stream comprising hydrogen and carbon monoxide and a stream comprising one or more olefins, and recovering the olefin(s), (c) combining the stream comprising hydrogen and carbon monoxide with the carbon dioxide removed from the product stream of step (a) and passing the resultant stream over a low temperature water gas shift catalyst to convert carbon dioxide and hydrogen into carbon monoxide and water, (d) passing carbon monoxide from step (c) and hydrogen to a Fischer-Tropsch reactor containing a Fischer-Tropsch catalyst wherein at least part of the carbon monoxide and hydrogen is converted to hydrocarbons, and thereafter recovering at least apart of the hydrocarbon product.

In this particular embodiment preferably no compression of the product stream is required. Consequently the main energy requirements are only those for separating the products and also for providing the oxygen-containing gas. We have found that these energy requirements can generally be satisfied by the heat supplied from cooling of the product stream and removal of the exothermic heat of reaction from the Fischer-Tropsch reactor. As a consequence, the overall process is essentially self-sufficient in energy and does not require the burning of any fuel. This results in the further advantage that as the carbon dioxide produced is consumed in the process, the process can be operated with the emission of little or no carbon dioxide, which is a substantial environmental benefit, particularly when compared with conventional steam cracking for example.

In all the embodiments of the present invention the autothermal cracking process as described in step (a) is operated at a pressure of greater than 15 barg. Preferably the autothermal cracking process is operated at a pressure of between 15-40 barg and advantageously between 20-30 barg e.g. 25 barg. It has been found that operating the autothermal cracking process between 15-20 barg surprisingly provides only a very small drop in olefin selectivity when compared to operating the autothermal cracking process at low pressure e.g. between 1-10 barg. Even more surprising is that when the pressure is increased to between 20-30 barg almost no further reduction in olefin selectivity is observed. Finally no additional loss in olefin selectivity occurs if the pressure is increased even further e.g. to between 30-40 barg.

In addition to passing the paraffinic hydrocarbon feedstock and the molecular oxygen-containing gas to the autothermal cracker, advantageously an additional feed stream comprising hydrogen may also passed to the autothermal cracker.

The paraffinic hydrocarbon feedstock may suitably be ethane, propane or butanes. It may be substantially pure or may be in admixture with other hydrocarbons and optionally other materials, for example methane, nitrogen, carbon monoxide, carbon dioxide, steam or hydrogen. A paraffinic hydrocarbon-containing fraction such as naphtha, gas oil, vacuum gas oil, or mixtures thereof may be employed. A suitable feedstock is a mixture of gaseous paraffinic hydrocarbons, principally comprising ethane, resulting from the separation of methane from natural gas. Another suitable feedstock is one comprising a C2-C4 mixture, e.g LPG comprising ethane as a minor component, which provides a product principally comprising a mixture of ethylene and propylene as the mono-olefin. Preferred is a paraffinic hydrocarbon principally comprising ethane which provides a product principally comprising ethylene as the mono-olefin.

It is preferred, although not essential, to preheat the paraffinic hydrocarbon feedstock to suitably between 50-450° C., preferably between 150-350° C.

As the molecular oxygen-containing gas there may suitably be used either oxygen or air. It is preferred to use oxygen, optionally diluted with an inert gas, for example nitrogen.

It is preferred, although not essential, to preheat the oxygen-containing gas to suitably between 50-250° C., preferably between 75-150° C.

It is preferred to pre-mix the oxygen-containing gas and the paraffinic hydrocarbon feedstock prior to contact with the autothermal cracking catalyst. In the presence of the autothermal cracking catalyst the composition of the paraffinic feedstock hydrocarbon/molecular oxygen-containing gas mixture is suitably from 3 to 15 times the stoichiometric ratio of hydrocarbon to oxygen-containing gas for complete combustion to carbon dioxide and water. The preferred composition is from 5 to 12 times the stoichiometric ratio of hydrocarbon to oxygen-containing gas.

Preferably the paraffinic feedstock and the molecular oxygen-containing gas are fed to the autothermal cracker in admixture under a Gas Hourly Space Velocity (GHSV) of greater than 80,000 $hr^{-1}$ in order to minimise the formation of carbon monoxide and carbon dioxide. Preferably, the GHSV exceeds 200,000 $hr^{-1}$, especially greater than 1,000,000 $hr^{-1}$. For the purposes of the present invention GHSV is defined as—vol. of total feed at STP/Time/(vol. of catalyst bed).

Regarding step (a) the autothermal cracking catalyst may be any catalyst capable of supporting combustion beyond the fuel rich limit of flammability. The catalyst may comprise a Group VIII metal as its catalytic component. Suitable Group VIII metals include platinum, palladium, ruthenium, rhodium, osmium and iridium. Rhodium, and more particularly, platinum and palladium are preferred. Typical Group VIII metal loadings range from 0.01 to 100 wt %, preferably, between 0.01 to 20 wt %, and more preferably, from 0.01 to 10 wt % based on the total dry weight of the catalyst.

Where a Group VIII catalyst is employed, it is preferably employed in combination with a catalyst promoter. The promoter may be a Group IIIA, IVA, and/or VA metal. Alternatively, the promoter may be a transition metal; the transition metal promoter being a different metal to that which may be employed as the Group VIII transition metal catalytic component.

Preferred Group IIIA metals include Al, Ga, In and Tl. Of these, Ga and In are preferred. Preferred Group IVA metals include Ge, Sn and Pb. Of these, Ge and Sn are preferred. The preferred Group VA metal is Sb. The atomic ratio of Group VIII B metal to the Group IIIA, IVA or VA metal may be 1:0.1-50.0, preferably, 1:0.1-12.0.

Suitable metals in the transition metal series include those metals in Group IB to VIII of the Periodic Table. In particular, transition metals selected from Groups IB, IIB, VIB, VIIB and VIII of the Periodic Table are preferred. Examples of such metals include Cr, Mo, W, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn. The atomic ratio of Group VIII metal to transition metal promoter may be 1:0.1-50.0, preferably, 1:0.1-12.0.

Preferably, the catalyst comprises only one promoter; the promoter being selected from Group IIIA, Group IVA, Group VB and the transition metal series. For example, the catalyst may comprise a metal selected from rhodium, platinum and palladium and a promoter selected from the group consisting of Ga, In, Sn, Ge, Ag, Au or Cu. Preferred examples of such catalysts include Pt/Ga, Pt/In, Pt/Sn, Pt/Ge, Pt/Cu, Pd/Sn, Pd/Ge, Pd/Cu and Rh/Sn. The Rh, Pt or Pd may comprise between 0.01 and 5.0 wt %, preferably, between 0.01 and 2.0 wt %, and more preferably, between 0.05 and 1.0 wt % of the total weight of the catalyst. The atomic ratio of Rh, Pt or Pd to the Group IIIA, IVA or transition metal promoter may be 1:0.1-50.0, preferably, 1:0.1-12.0. For example, atomic ratios of Rh, Pt or Pd to Sn may be 1:0.1 to 50, preferably, 1:0.1-12.0, more preferably, 1:0.2-3.0 and most preferably, 1:0.5-1.5. Atomic ratios of Pt or Pd to Ge, on the other hand, may be 1:0.1 to 50, preferably, 1:0.1-12.0, and more preferably, 1:0.5-8.0. Atomic ratios of Pt or Pd to Cu may be 1:0.1-3.0, preferably, 1:0.2-2.0, and more preferably, 1:0.5-1.5.

Alternatively, the promoter may comprise at least two metals selected from Group IIIA, Group IVA and the transition metal series. For example, where the catalyst comprises platinum, the platinum may be promoted with two metals from the transition metal series, for example, palladium and copper. Such Pt/Pd/Cu catalysts may comprise palladium in an amount of 0.01 to 5 wt %, preferably, 0.01 to 2 wt %, and more preferably, 0.01 to 1 wt % based on the total weight of the dry catalyst. The atomic ratio of Pt to Pd may be 1:0.1-10.0, preferably, 1:0.5-8.0, and more preferably, 1:1.0-5.0. The atomic ratio of platinum to copper is preferably 1:0.1-3.0, more preferably, 1:0.2-2.0, and most preferably, 1:0.5-1.5.

Where the catalyst comprises platinum, it may alternatively be promoted with one transition metal, and another metal selected from Group IIIA or Group IVA of the periodic table. In such catalysts, palladium may be present in an amount of 0.01 to 5 wt %, preferably, 0.01 to 2.0 wt %, and more preferably, 0.05-1.0 wt % based on the total weight of the catalyst. The atomic ratio of Pt to Pd may be 1:0.1-10.0, preferably, 1:0.5-8.0, and more preferably, 1:1.0-5.0. The atomic ratio of Pt to the Group IIIA or IVA metal may be 1:0.1-60, preferably, 1:0.1-50.0. Preferably, the Group IIIA or IVA metal is Sn or Ge, most preferably, Sn.

For the avoidance of doubt, the Group VIII metal and promoter in the catalyst may be present in any form, for example, as a metal, or in the form of a metal compound, such as an oxide.

It should be understood that actual concentrations of metal in the catalysts tend not to be identical to the nominal concentrations employed in the preparation of the catalyst because not all the metal employed during the preparation of the catalyst actually becomes incorporated in the catalyst composition. Thus, the nominal metal concentrations may have to be varied to ensure that the desired actual metal concentrations are achieved.

The autothermal cracking catalyst may be unsupported, such as in the form of a metal gauze, but is preferably supported. Any suitable support may be used such as ceramic or metal supports, but ceramic supports are generally preferred. Where ceramic supports are used, the composition of the ceramic support may be any oxide or combination of oxides that is stable at high temperatures of, for example, between 600° C. and 1200° C. The support material preferably has a low thermal expansion coefficient, and is resistant to phase separation at high temperatures.

Suitable ceramic supports include corderite, lithium aluminium silicate (LAS), alumina ($\alpha$-$Al_2O_3$), yttria stabilised zirconia, alumina titanate, niascon, and calcium zirconyl phosphate. The ceramic supports may be wash-coated, for example, with $\gamma$-$Al_2O_3$.

The autothermal cracking catalyst may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support may then be reduced, for example, by heat treatment in a hydrogen atmosphere.

The reaction in step (a) may be suitably carried out at a catalyst exit temperature of between 800° C. and 1200° C., preferably between 850° C. and 1050° C.

The reaction products are preferably quenched as they emerge from the reaction chamber to avoid further reactions taking place. This maintains the degree of olefin selectivity. The heat from the quenching may be used to generate high-pressure steam, which could be used to provide power for those parts of the overall process requiring it.

The time at which the product stream is maintained at the autothermal cracking temperature is defined as the residence time. As the operating pressure is increased the residence time must be decreased to maintain the olefin selectivity.

Preferably the product stream is quenched by injection of a large volume of nitrogen at a temperature of approximately 25° C. This nitrogen injection reduces the temperature of the product stream such that the temperature of the stream is reduced from the autothermal cracking temperature of between 800° C. and 1200° C. to a temperature between 750-600° C. Below this temperature the gas phase reactions are reduced to such an extent that no change in the product distribution occurs.

The residence times are calculated using the formulae $$\text{Residence time (milliseconds)} = 1000 \times \frac{\text{Reaction volume } R \text{ (cm}^3\text{)}}{\text{Gas volume } V \text{ (cm}^3/\text{s)}}$$

wherein
R is the volume of catalyst plus the volume of space between the catalyst exit face and the plane of the quench injection
V is the volume of the gas stream passing through the reaction zone calculated from the gas feed rates, reaction temperature and test pressure using the formula below.

$$\text{Gas volume} = M \times \text{Feed flow to reactor } F \text{ (nl/min)} \times \frac{1}{(1+P)} \times \frac{(273+T)}{273}$$

wherein
M is a molecular expansion factor corresponding to the volumetric increase associated with the autothermal reaction (moles of product gas=M×moles of feed). (M varies with feed composition but for ethane autothermal cracking is taken as 1.4) F is the volumetric flow rate into the reaction zone measured in normal liters per minute (F excludes quench nitrogen flow)

P is the test pressure measured in barg and

T is the temperature of autothermal reaction, and for the purposes of the calculation is taken to be the catalyst exit temperature measured in ° C.

Usually the product stream is cooled to between 750-600° C. within less than 100 milliseconds of formation, preferably within 50 milliseconds of formation and most preferably within 20 milliseconds of formation e.g. within 10 milliseconds of formation.

Wherein step (a) is operated at a pressure of 15-20 barg usually the products are quenched and the temperature cooled to between 750-600° C. within 20 milliseconds of formation. Advantageously wherein step (a) is operated at a pressure of greater than 20 barg the products are quenched and the temperature cooled to between 750-600° C. within 10 milliseconds of formation.

The percentage of conversion of paraffinic hydrocarbon in step (a) is usually greater than 50%, preferably greater than 60%, and most preferably greater than 70%.

Furthermore the selectivity towards olefins is usually greater than 30%, preferably greater than 40%, and most preferably greater than 50%.

Any coke produced in the autothermal cracking process may be removed by mechanical means, or by using one of the decoking methods such as that described in EP-A-0709446, the contents of which are hereby incorporated by reference.

For further details of preferred methods of operation reference may be made to the aforesaid EP-B1-0332289; EP-B1-0529793; and EP-A-0709446.

The product stream may be passed to at least one heat exchanger wherein the stream is cooled to a temperature approaching the dew point of the stream at a pressure of between 15 and 40 barg. The heat from the heat exchanger may be used to generate high-pressure steam, which may be used to provide power for those parts of the overall process requiring it.

Wherein the downstream separation is based on a conventional refrigerated distillation separation the product stream may be compressed to a pressure between 15 and 40 barg to facilitate the separation of the products. Advantageously this may not be necessary when the step (a) is operated at a sufficiently high pressure to preclude the need for compression.

Wherein carbon dioxide is removed from the product stream of step (a) the carbon dioxide may be removed by a range of conventional carbon dioxide removal systems such as liquid absorbents, solid adsorbents, and polymer membranes. The carbon dioxide may be removed using an amine-based absorption system such as MEA or TEA (or mixtures of both), or any other commercially available carbon dioxide removal process. Typically the carbon dioxide can be reduced to below 50 ppmv by the use of an amine removal system consisting of a high pressure absorber column which contacts the product stream with an amine solution.

Typically the product stream is contacted with the amine solution at a pressure of greater than 15 barg and a temperature of less than 50° C. Suitable amines include diglycolamine (DGA), monoethanolamine (MEA), methyldiethanolamine (MDEA) and diethanolamine (DEA) and are usually utilised as aqueous solutions with concentrations in the range of 10-50 wt %.

In step (b) of the present invention the product from step (a) is separated into a stream comprising carbon monoxide, hydrogen and optionally methane and a stream and comprising one or more mono-olefin(s). The mono-olefin(s) are treated and recovered. The product stream is usually separated into a C2+ stream, and a light gas stream comprising components lighter than ethylene. The preferred method of achieving this is to use a distillation column operating at 20-40 barg, preferably operating at 25-35 barg with an overhead temperature of −100 to −180° C.

The light gas stream comprising components lighter than ethylene may be separated into a hydrogen rich stream and a methane rich stream by partial condensation. Carbon monoxide may also be recovered by further distillation or absorption using a solvent such as liquid methane.

The C2+ stream may then be separated into the olefin products and paraffin streams (which may be recycled back to step (a)). Selective hydrogenation may then be used to selectively convert unsaturated compounds such as acetylenes, propadiene and unrecovered dienes to the associated olefin or paraffin.

In step (c) of the third embodiment of the invention the stream comprising carbon monoxide and hydrogen separated in step (b) is usually combined with the carbon dioxide separated from the product stream of step (a). The hydrogen/carbon monoxide molar ratio is usually between 1.8:1 and 2.1:1. The stream is then passed over a catalyst for the water gas shift reaction. The water gas shift reaction may be represented as the equilibrium:

$$CO + H_2O \rightleftharpoons CO_2 + H_2 \qquad (I)$$

In this particular case it is used to convert carbon dioxide to carbon monoxide by consuming hydrogen. The water gas shift reaction is well-known in the art. It is generally operated in the presence of a catalyst; typically an iron oxide catalyst may be employed, although other catalysts known in the art may equally be used. Temperatures typically in the range from 350 to 500° C. may suitably be used. The product stream from this reaction contains water, carbon monoxide and residual hydrogen, in addition to a small amount of carbon dioxide. Optionally any excess hydrogen over that required for the following step may be separated off, e.g. using a polymeric membrane.

The Fischer-Tropsch process produces hydrocarbons from $C_1$ upwards, but principally in the $C_5$-$C_{60}$ range. In recent years attention has been directed to the Fischer-Tropsch process as one of the more attractive direct and environmentally acceptable routes to high quality transportation fuels from alternative energy sources such as coal and natural gas via intermediate formation of synthesis gas (carbon monoxide and hydrogen).

The catalyst for the Fischer-Tropsch reaction may suitably comprise at least one metal selected from cobalt, nickel, iron, molybdenum, tungsten, thorium, ruthenium, rhenium, and platinum. Of the aforesaid metals cobalt, nickel and iron are preferred. Generally, the metals may be used in combination with a support material. Suitable support materials include alumina, silica and carbon, and mixtures of two or more thereof. The use of cobalt, for example, as a catalytically active metal in combination with a support is well-known from, for example EP-A-127220; EP-A-142887; GB-A-2146350; GB-A-2130113; EP-A-0209980; EP-A-0261870 and GB-A-2125062. Of these EP-A-127220, for example, discloses the use of a catalyst comprising (i) 3-60 pbw cobalt, (ii) 0.1-100 pbw zirconium, titanium, ruthenium or chromium, per 100 pbw silica, alumina or silica-alumina, (iii) the catalyst having been prepared by kneading and/or impregnation. EP-A-0209980 describes the use in the conversion of synthesis gas to hydrocarbons of a catalyst having a composition represented by the formula:

wherein A is an alkali metal
a is greater than zero and up to 25% w/w,
b is in the range from zero to 5% w/w,
c is in the range from zero to 15% w/w,
x is a number such that the valence requirements of the other elements for oxygen is satisfied, and the remainder of the composition, subject to the requirement for x, is cerium.

EP-A-0261870 discloses a composition for use after reductive activation as a catalyst in the conversion of synthesis gas to hydrocarbons, which composition comprises as essential components (i) cobalt either as the elemental metal, the oxide or a compound thermally decomposable to the elemental metal and/or oxide and (ii) zinc in the form of the oxide or a compound thermally decomposable to the oxide.

Fischer Tropsch conditions are suitably a temperature in the range from 160 to 350° C., preferably from 180 to 275° C., and a pressure in the range from 0 to 100 barg, preferably from 5 to 50 barg e.g. 1 5-40 barg. The GHSV for continuous operation may suitably be in the range from 100 to 25000 h$^{-1}$.

The Fischer-Tropsch process may be carried out batchwise or continuously, preferably continuously, in a fixed bed, fluidised bed or slurry phase reactor. The Fischer-Tropsch process produces syncrude and a fuel gas. Any residual carbon dioxide in the fuel gas can be removed, for example by passing the gas, together with any excess hydrogen, through a methanation stage. Heat from the reaction is used to produce a high pressure steam, which may be used to generate power for other parts of the process.

The invention will now be further described by reference to FIGS. 1-3.

Figure 1:
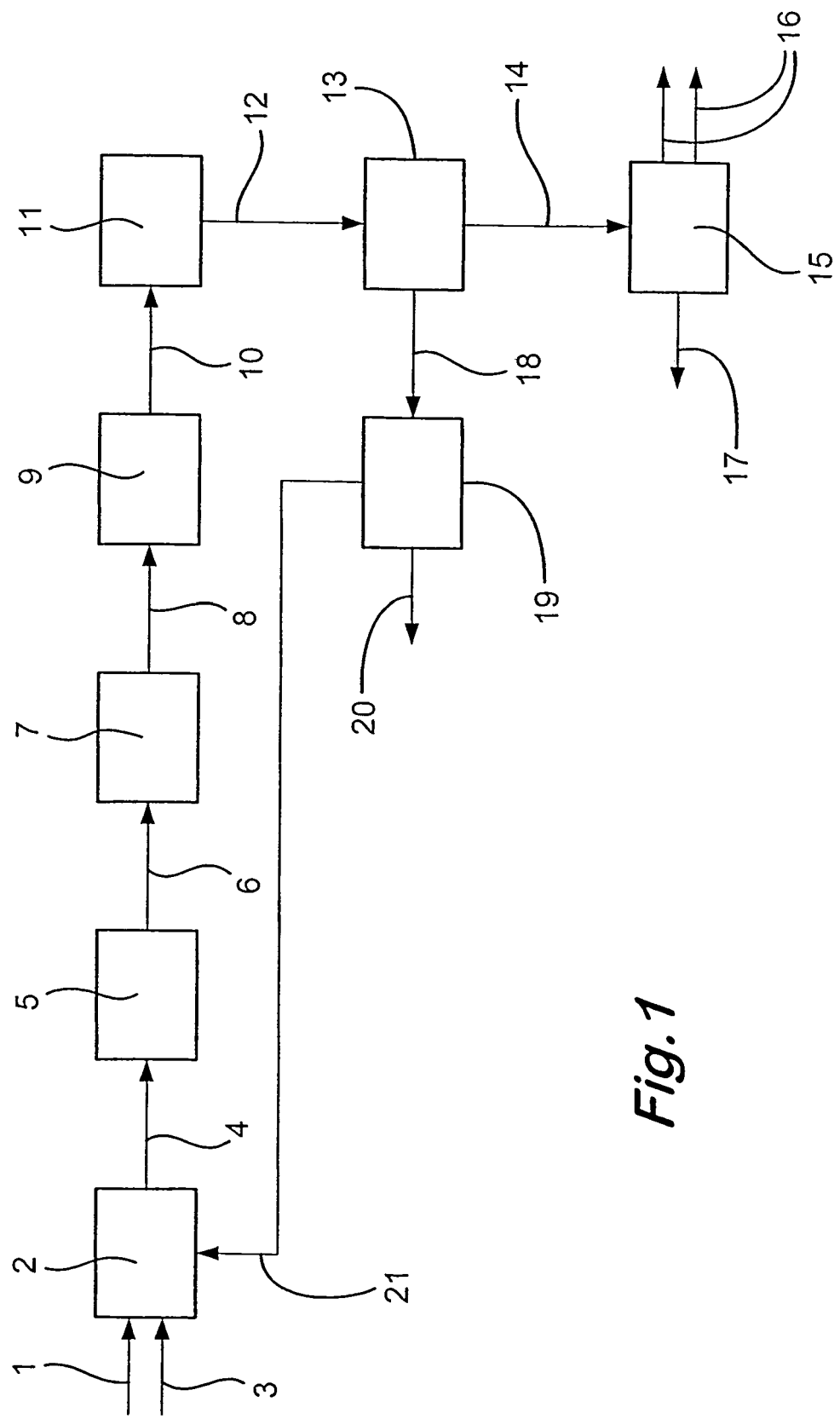
FIG. 1 is a schematic diagram of the overall process.

In FIG. 1 a high pressure paraffinic hydrocarbon feedstock, principally comprising ethane, is fed through line (1) to an autothermal cracker (2). Also fed to the autothermal cracker through line (3) is oxygen. The autothermal cracker (2) is maintained under conditions whereby the reaction is effected to produce a product stream comprising ethylene, higher olefins, methane, carbon dioxide, carbon monoxide and hydrogen. The product stream exits the autothermal cracker (2) via line (4) and is passed to a heat exchanger (5) wherein the stream is cooled. The cooled product stream then passes via line (6) to an oxygenate removal zone (7) wherein oxygenates are removed from the cooled product stream. The cooled product stream then passes via line (8) to a carbon dioxide removal zone (9). The cooled product stream exits the carbon dioxide removal zone (9) and passes via line (10) to a polishing zone (11) wherein the stream is passed through an adsorbent bed (e.g. alumina) to remove the remaining carbon dioxide, moisture and any oxygenated compounds such that the stream is suitable for refrigerated distillation at cryogenic temperatures. The cooled product stream then passes via line (12) to a demethanisation zone (13) wherein the cooled product stream is separated into a C2+ stream and a light gas stream comprising components lighter than ethylene.

The light gas stream comprising components lighter than ethylene then passes via line (14) to a light gas purification zone (15) wherein the light gas stream comprising components lighter than ethylene is separated into a hydrogen rich stream which exits the light gas purification zone (15) via line (16) and a methane rich stream which exits the light gas purification zone (15) via line (17).

The C2+ stream passes via line (18) from the demethanisation zone (13) into a product separation zone (19) wherein the C2+ stream is separated into an olefin product stream which exits the product separation zone (19) via line (20) and a paraffin stream which exits the product separation zone (19) via line (21) which is then recycled back to the autothermal cracker (2).

Figure 2:
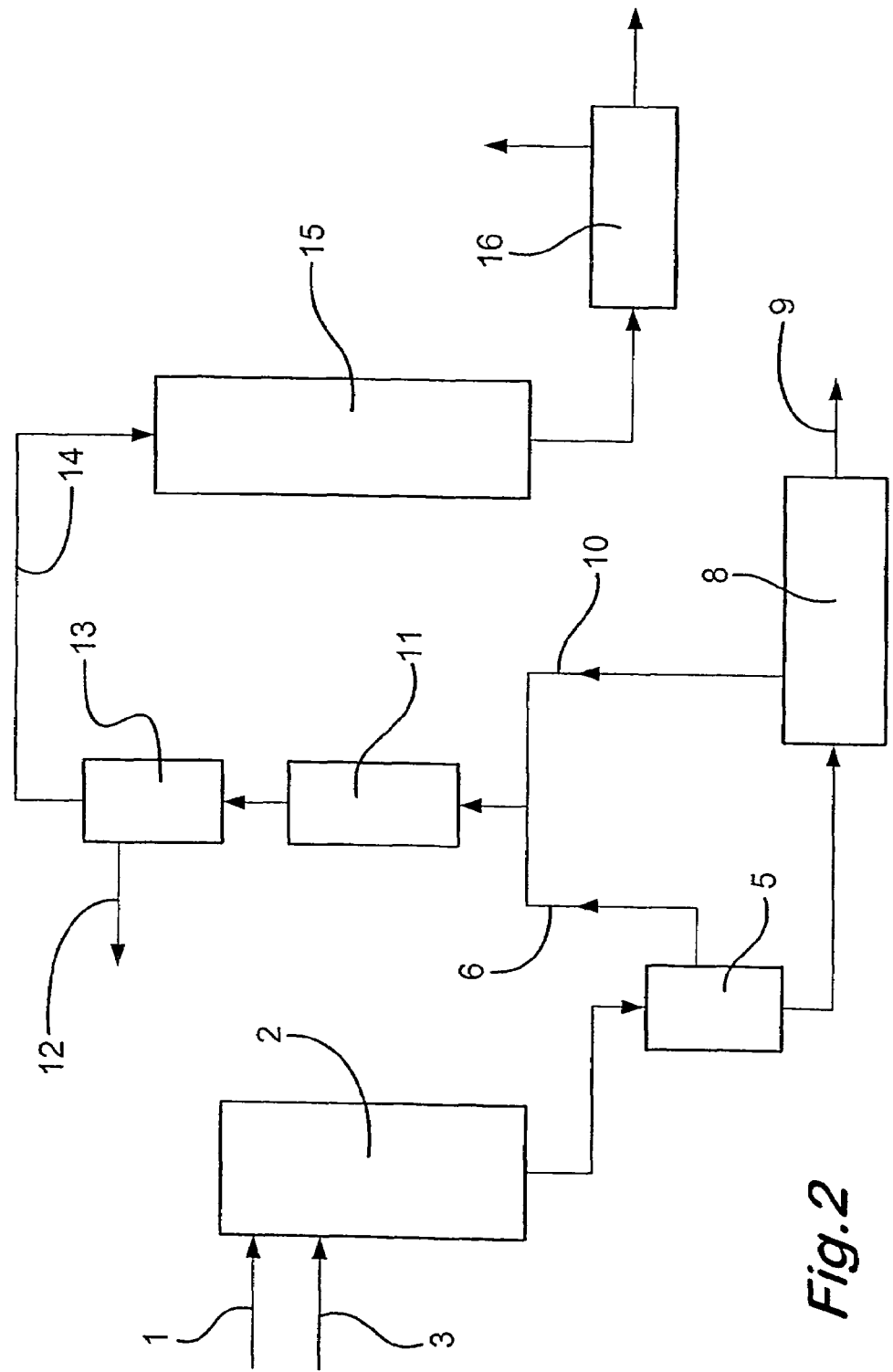
FIG. 2 is an embodiment of the process.
Figure 3:
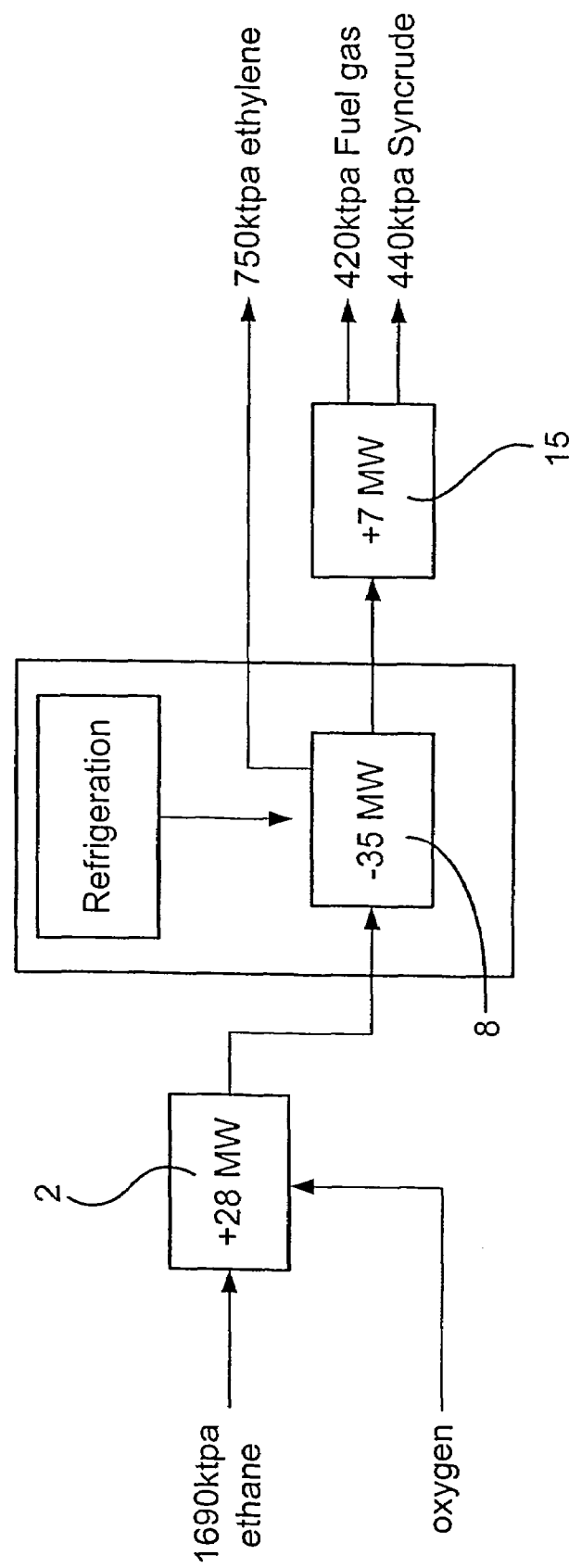
FIG. 3 is a cryogenic separation powered by stream from Fischer-Tropsch reaction.

In FIG. 2 a high pressure paraffinic hydrocarbon feedstock, principally comprising ethane, is fed through via line (1) to the autothermal cracker (2). Also fed to the autothermal cracker (2) via line (3) is oxygen. The autothermal cracker (2) is maintained under conditions whereby the reaction is effected to produce ethylene, higher olefins, methane, carbon dioxide, carbon monoxide and hydrogen. The product is passed via line (4) to an initial separation zone (5) where carbon dioxide is removed from the stream using an amine absorption system and exits the initial separation zone via line (6).

The remaining mixture is passed via line (7) to a further separation zone (8) wherein the carbon monoxide, hydrogen and methane is separated cryogenically from ethylene and higher olefins. The ethylene and higher olefins are removed from the further separation zone (8) via line (9) for treatment and recovery in the normal way. The mixture of carbon monoxide, hydrogen and methane exits the further separation zone (8) via line (10) and is mixed with the previously separated carbon dioxide (line (6)) and then passed over a water gas shift catalyst in reactor (11), in order to convert carbon dioxide to carbon monoxide by consuming hydrogen. Optionally any excess hydrogen over that required for the subsequent Fischer-Tropsch reaction may be separated off the through line (12) using a polymeric membrane (13).

The remaining mixture of carbon monoxide, hydrogen and methane is fed via line (14) to the Fischer-Tropsch reactor (15). In reactor (15) carbon monoxide and hydrogen is converted to a mixture of fuel gas and syncrude which is separated in separator (16) and recovered.

Heat from the Fischer-Tropsch reaction is used to produce high pressure steam, which can be further superheated by the autothermal cracking reaction itself, and which is used to contribute power for the refrigeration unit in the cryogenic separator. This is shown in FIG. 3, which shows the energy balance for the system of FIG. 2. The heat generated by the autothermal cracking reaction itself in reactor (2) provides 28 MW of power in this embodiment, whilst the Fischer-Tropsch reactor (15) generates 7 MW. This exactly matches the 35 MW required for the cryogenic separation (8) of the products of the autothermal cracking reaction. Hence the overall system is self-sufficient in energy, and does not require the burning of any fuel. This is advantageous not only because of the obvious benefit of improved economics, but also because of the absence of any fuel burning means that no carbon dioxide is produced.

The invention will now be illustrated using the following examples;

EXAMPLE 1

Figure 4:
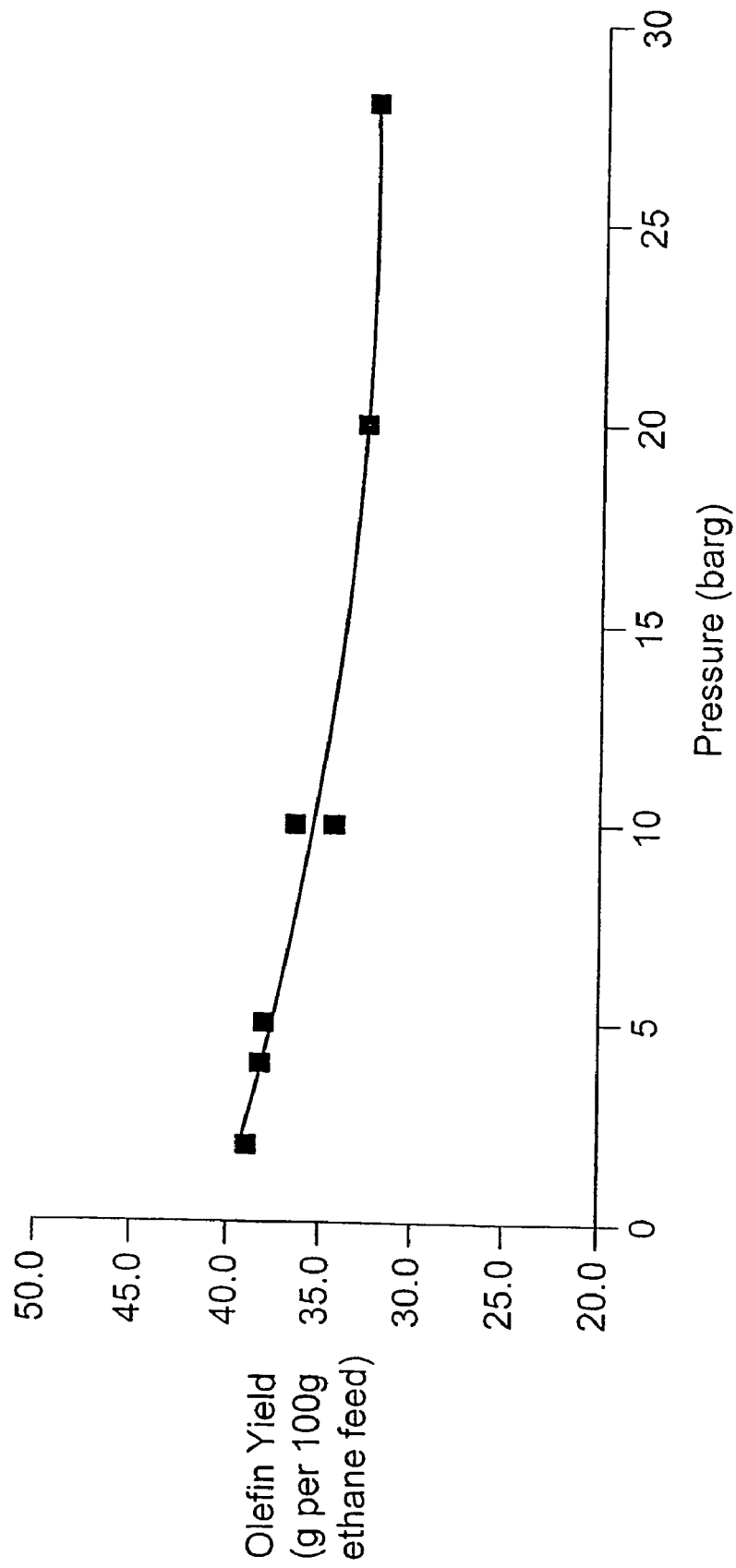
FIG. 4 is a variation of olefin yield with pressure.

The effect of pressure on olefin yield was determined wherein the conversion rate of ethane was maintained at approximately 60%. Ethane and oxygen was preheated to a temperature of between 130-220° C. and passed to an autothermal cracking reactor. The ethane and oxygen was contacted with a platinum on alumina catalyst. The autothermal cracking reactor was maintained at a temperature of between 850-950° C. and the pressure was varied between 2-28 barg. The product stream was quenched with nitrogen and the olefin yield was determined. The results are shown in table 1 and FIG. 4 shows a plot of the olefin yield versus pressure. It can be seen from FIG. 4 that the loss in olefin selectivity between 15-20 barg is less than expected when compared to an extrapolation of the data at low pressure e.g. 1-10 barg and that the loss in olefin selectivity between 20-28 barg is negligible.

EXAMPLE 2

Figure 5:
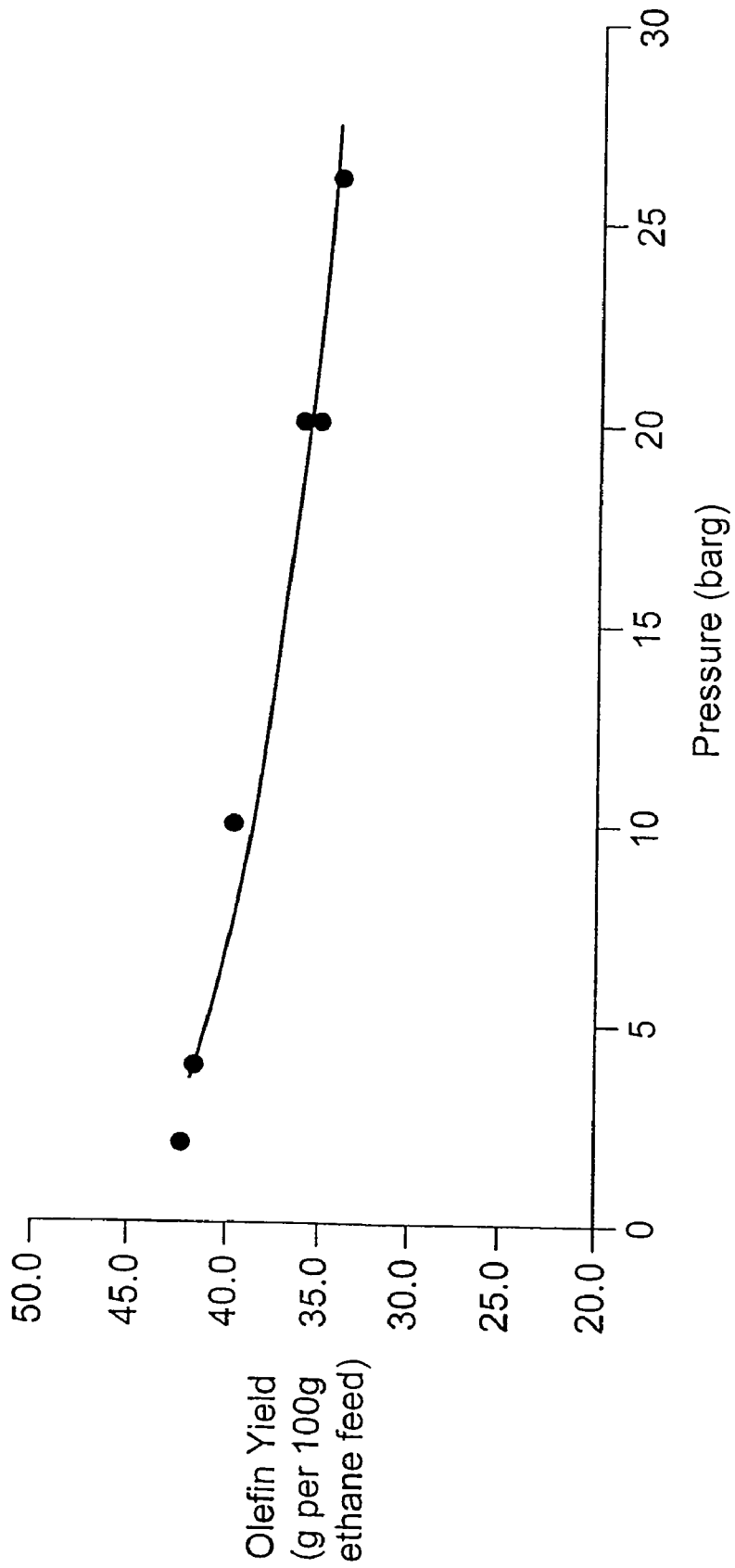
FIG. 5 is a variation of olefin yield with pressure.

Example 1 was repeated however the effect of pressure on olefin yield was determined wherein the conversion rate of ethane was maintained at approximately 70%. Ethane and oxygen was preheated to a temperature of between 130-220° C. and passed to an autothermal cracking reactor. The ethane and oxygen was contacted with the platinum on alumina catalyst. The autothermal cracking reactor was maintained at a temperature of between 920-990° C. and the pressure was varied between 2-26 barg. The product stream was quenched with nitrogen and the olefin yield was determined. The results are shown in table 2 and FIG. 5 shows a plot of the olefin yield versus pressure. It can be seen from FIG. 5 that again the loss in olefin selectivity between 15-20 barg is less than expected and that the loss in olefin selectivity between 20-26 barg is minimal.

TABLE 1

OLEFIN YIELD AT 60% ETHANE CONVERSION

| PRESSURE BARG | PREHEAT TEMP | REACTOR TEMP | FEED RATES | | | | RESIDENCE | | OLEFIN YIELD [C2 = PLUS C3 =] G/100 G C2 FEED |
|---|---|---|---|---|---|---|---|---|---|
| | | | ETHANE G/MIN | OXYGEN G/MIN | NITROGEN G/MIN | QUENCH NITROGEN G/MIN | TIME TO QUENCH MS | ETHANE CONVERSION | |
| 2 | 129 | 933 | 38.16 | 16.85 | 3.50 | 6.90 | 15.5 | 63.13 | 38.71 |
| 4 | 144 | 931 | 65.17 | 26.71 | 3.50 | 7.81 | 15.9 | 62.82 | 38.07 |
| 5 | 152 | 900 | 48.68 | 21.13 | 11.08 | 99.99 | 10.3 | 59.54 | 37.80 |
| 10 | 169 | 849 | 47.78 | 20.73 | 15.99 | 9.32 | 27.3 | 58.69 | 34.21 |
| 10 | 211 | 931 | 103.12 | 40.95 | 26.84 | 40.12 | 12.3 | 60.44 | 36.20 |
| 20 | 140 | 907 | 177.42 | 69.37 | 45.11 | 73.78 | 10.7 | 60.20 | 32.75 |
| 28 | 138 | 900 | 165.90 | 67.37 | 23.32 | 236.25 | 9.1 | 61.39 | 32.47 |

TABLE 2

OLEFIN YIELD AT 70% ETHANE CONVERSION No. H2 CO-FEED

| PRESSURE BARG | PREHEAT TEMP | REACTOR TEMP | FEED RATES | | | | RESIDENCE | | OLEFIN YIELD [C2 = PLUS C3 =] G/100 G C2 FEED |
|---|---|---|---|---|---|---|---|---|---|
| | | | ETHANE G/MIN | OXYGEN G/MIN | NITROGEN G/MIN | QUENCH NITROGEN G/MIN | TIME TO QUENCH MS | ETHANE CONVERSION | |
| 2 | 128 | 951 | 37.16 | 17.72 | 3.50 | 7.07 | 15.3 | 69.8 | 41.99 |
| 4 | 162 | 950 | 63.63 | 28.34 | 4.33 | 8.38 | 15.5 | 70.5 | 41.22 |
| 10 | 180 | 926 | 93.68 | 42.55 | 25.31 | 40.10 | 13.4 | 69.8 | 39.27 |
| 20 | 209 | 983 | 100.10 | 41.92 | 11.10 | 99.70 | 13.8 | 68.9 | 35.65 |
| 20 | 120 | 937 | 150.47 | 69.95 | 11.06 | 145.35 | 123 | 67.0 | 34.70 |
| 26 | 163 | 925 | 205.47 | 100.00 | 24.39 | 151.74 | 121 | 68.0 | 33.72 |

The invention claimed is:

1. A process for the production of a mono-olefin from a feedstock comprising a paraffinic hydrocarbon which process comprises
   a) partially combusting at a pressure of 15 to 28 barg a mixture of the selected from the group consisting of ethane, propane, butane(s) and mixtures thereof; hydrocarbon feed and a molecular oxygen-containing gas in contact with a catalyst capable of supporting combustion beyond the normal fuel rich limit of flammability where they are reacted to form a product comprising one or more mono-olefin(s), carbon monoxide and hydrogen and
   b) separating at a pressure of at least 15 barg the product from step (a) into a stream comprising carbon monoxide and hydrogen and a stream comprising one or more olefins and recovering the one or more olefin(s);
   wherein the product produced in step (a) comprises carbon dioxide, wherein prior to step (b) the carbon dioxide is removed from the product stream and wherein the selectivity to olefin is at least 55%.

2. A process according to claim 1 comprising step (c) passing the stream comprising carbon monoxide and hydrogen separated in step (b) to a Fischer-Tropsch reactor containing a Fischer-Tropsch catalyst wherein at least part of said stream is converted to hydrocarbons, and thereafter recovering at least a part of the hydrocarbon product.

3. A process according to claim 2 wherein the product produced in step (a) comprises one or more mono-olefin(s), carbon monoxide, hydrogen and methane and step (b) separates the product from step (a) into a stream comprising carbon monoxide, hydrogen and methane which is then passed to the Fischer-Tropsch reactor in step (c).

4. A process according to claim 1 which comprises removing carbon dioxide from the product stream of step (a),
   (b) separating the product stream of step (a) into a stream comprising hydrogen and carbon monoxide and a stream comprising one or more olefins, and recovering the olefin(s),
   (c) combining the stream comprising hydrogen and carbon monoxide with the carbon dioxide removed from the product stream of step (a) and passing the resultant stream over a low temperature water gas shift catalyst to convert carbon dioxide and hydrogen into carbon monoxide and water,
   (d) passing carbon monoxide from step (c) and hydrogen to a Fischer-Tropsch reactor containing a Fischer-Tropsch catalyst wherein at least part of the carbon monoxide and hydrogen is converted to hydrocarbons, and thereafter recovering at least a part of the hydrocarbon product.

5. A process according to claim 1 wherein an additional co-feed of hydrogen is used in step (a).

6. A process according to claim 1 wherein the paraffinic hydrocarbon feedstock is ethane.

7. A process according to claim 1 wherein the paraffinic hydrocarbon feedstock is preheated to a temperature of between 50-450° C.

8. A process according to claim 1 wherein the molecular oxygen containing gas is preheated to a temperature of between 50-250° C.

9. A process according to claim 1 wherein the molecular oxygen-containing gas is pre-mixed with the paraffinic hydrocarbon feedstock prior to contact with the catalyst.

10. A process according to claim 1 wherein step (a) is operated at an elevated pressure of at least 20 barg.

11. A process according to claim 1 wherein step (a) is operated at a temperature greater than 500° C.

12. A process according to claim 1 wherein the carbon dioxide is removed from the product stream of step (b) using an amine-based absorption system.

13. A process according to claim 4 wherein the low temperature water gas shift catalyst is an iron oxide catalyst.

14. A process according to claim 4 wherein the stream comprising carbon monoxide and hydrogen is combined with the carbon dioxide and passed over the low temperature water gas shift catalyst at a temperature between 350-500° C.

15. A process according to claim 2 wherein the stream comprising carbon monoxide and hydrogen which is passed to the Fischer-Tropsch reactor has a hydrogen/carbon monoxide molar ratio between 1.8:1 to 2.1:1.

16. A process according to claim 2 wherein the stream comprising carbon monoxide and hydrogen is passed over the Fischer-Tropsch catalyst at a temperature between 160-350° C.

17. A process according to claim 2 wherein the stream comprising carbon monoxide and hydrogen is passed over the Fischer-Tropsch catalyst at a pressure between 15-40 barg.

18. A process according to claim 2 wherein the Fischer-Tropsch reaction is carried out batchwise or continuously, in a fixed bed, fluidised bed or slurry phase reactor.

19. A process according to claim 12 wherein the amine-based absorption system is MEA, TEA or mixtures of both.

* * * * *